United States Patent [19]

Marsh

[11] 4,226,783
[45] Oct. 7, 1980

[54] α-CHLORINATION PROCESS

[75] Inventor: Frank D. Marsh, Wilmington, Del.

[73] Assignee: E. I. Du Pont de Nemours and Company, Wilmington, Del.

[21] Appl. No.: 921,382

[22] Filed: Jul. 3, 1978

[51] Int. Cl.$^3$ .................. C07C 50/16; C07C 21/24; C07C 50/24; C07B 9/00
[52] U.S. Cl. .................. 260/351; 260/694; 560/109; 260/649 R; 560/130; 560/142; 260/384; 260/509; 260/510; 260/505 R; 260/465 G; 560/144; 260/410.5; 560/227; 260/456 A; 260/456 P; 260/511; 260/508; 560/227; 568/323; 260/920; 568/28; 570/144; 570/196
[58] Field of Search ........... 260/694, 384, 351, 649 R, 260/651 R, 651 HA

[56] References Cited

U.S. PATENT DOCUMENTS

| | | | |
|---|---|---|---|
| 893,507 | 7/1908 | Isler | 260/384 |
| 2,010,841 | 8/1935 | Bender | 260/694 |
| 2,046,411 | 7/1936 | Ramage | 260/694 |
| 2,926,201 | 2/1960 | Dreisbach et al. | 260/651 |
| 3,271,465 | 9/1966 | Krewer et al. | 260/649 R |
| 3,449,421 | 6/1969 | Pearson | 260/694 |

OTHER PUBLICATIONS

*Chemical Abstracts*, vol. 19, p. 7031, "Action of Chlorine Monoxide on Organic Compounds," Goldshimidt et al., 1925.
*Organic Chemistry*, Third Edition, 1975, Morrison & Boyd, pp. 386-388, Allyl & Bacon Inc., Boston.
*Jol. of American Chemical Society*, vol. 89(1), pp. 121-125, "Radical Chain Halogenation Reactions of Chlorine Monoxide," Tanner & Nychka, 1966.
*Chemical Abstracts*, vol. 42, p. 1948, Abstract No. 6626a, "Correlation of Rates of Halogenation of Methyl Benzenes," London, 1948.
*Chemical Abstracts*, vol. 55, p. 1961, Abstract no. 19849c, "The Chlorination of N,N-Dimethylaniline," Chao & Cipriani, 1961.
*Chemical Abstracts*, vol. 55, Abstract No. 14026a, "Relative Reaction Activity of Some Alkylaromatic Hydrocarbons in Photochemical Chlorination," Cerny & Hajek, 1961.

*Primary Examiner*—Winston A. Douglas
*Assistant Examiner*—Raymond K. Covington

[57] ABSTRACT

A process for α-chlorination of side chains of electronegatively substituted aromatic compounds with dichlorine monoxide.

9 Claims, No Drawings

α-CHLORINATION PROCESS

BACKGROUND OF THE INVENTION

This invention relates to chlorination with dichlorine monoxide which compound is commonly referred to in the literature as chlorine monoxide.

*Chem. Rev.* 76,487 (1976) discloses reaction of various organic compounds with chlorine monoxide.

U.S. Pat. No. 3,872,176 discloses preparation of 1,1,1-trichloroethane by reaction of chlorine monoxide with chloroethane or 1,1-dichloroethane.

None of the above publications discloses α-chlorination of a side chain on an aromatic compound.

SUMMARY OF THE INVENTION

This invention is directed to a process for α-chlorination of a side chain of an electronegatively substituted aromatic compound such as within the scope of formulae I-V with dichlorine monoxide ($Cl_2O$).

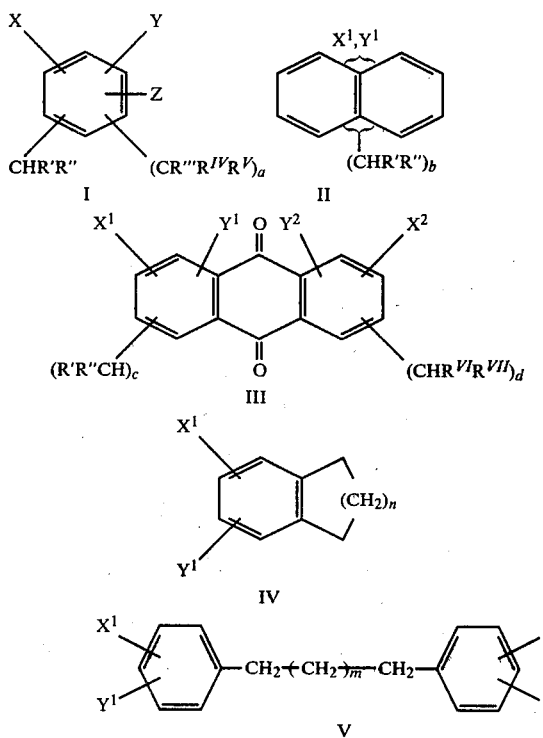

wherein for Formula I:
X is $NO_2$, CN, $CF_3$, Cl, Br, F,

$SO_2R_2$, $SO_3R_2$, $SO_2CF_3$, $SO_2Cl$, $SO_2NR_3R_4$, $$OCR_5 \overset{O}{\overset{\|}{}}, \; \overset{\oplus}{N(R_2)_3}, \; NR_6CR_2 \overset{O}{\overset{\|}{}}, \; \overset{\oplus}{P(R_2)_3}, \; P(OR_2)_2 \overset{O}{\overset{\|}{}}$$

or $CCl_3$;
Y is H, $NO_2$, Cl, Br, F, CN, $CF_3$,

$SO_2R_2$, $SO_3R_2$, $SO_2NR_3R_4$, $OCF_3$,

$OR_6$ or aryl;
Z is H, Cl or Br;
and for Formulae II-V;
$X^1$ and $X^2$ are independently $NO_2$, CN, $CF_3$, Cl, BR, F,

$SO_2R_2$, $SO_3R_2$, $SO_2CF_3$, $SO_2Cl$, $SO_2NR_3R_4$,

or $CCl_3$ or can be H for Formula III;
$Y^1$ and $Y^2$ are independently H, $NO_2$, Cl, Br, CN or

wherein in Formula I to V,
$R_1$ is alkyl of 1-8 carbons, aryl, alkoxy of 1-4 carbons, OH or $NR_3R_4$;
$R_2$ is alkyl of 1-4 carbons;
$R_3$ and $R_4$ are independently H or alkyl of 1-4 carbons;
$R_5$ is alkyl of 1-8 carbons, trifluoromethyl, or aryl;
$R_6$ is H or alkyl of 1-3 carbons; and furthermore,
R' and R" are independently H, alkyl of 1-3 carbons, or are joined to form a carbocyclic ring of 5 or 6 carbons; and for R', it can also be alkyl of 1-20 carbon atoms;
R''', $R^{IV}$ and $R^V$ are independently H or methyl;
$R^{VI}$ and $R^{VII}$ are independently H, alkyl of 1-3 carbon or are joined to form a carbocyclic ring of 5 or 6 carbons;
a is 0 or 1;
b, and c are independently 1 or 2;
n is 1 or 2; d is 0, 1, or 2; m is 0-6.

In formula II, it is understood that $X^1$ and $Y^1$ can be in the same or different ring nucleus; also in formula II it is understood that when b is 2, each of the two identical CHR'R" groups can be on the same or different ring nucleus.

DETAILED DESCRIPTION OF THE INVENTION

Compounds of Narrower Scope

α-chlorinated compounds of a narrower scope are formed from compounds of formulae I-V where:
for formula I:
X is $NO_2$, Cl, Br, CN, $CF_3$,

$SO_2R_2$, $SO_2NR_3R_4$, $SO_3R_2$,

or $CCl_3$;

Y is H, $NO_2$, Cl, Br, CN, $CF_3$,

$SO_3R_2$ or $OR_6$;

Z is H, Cl or Br;

and for Formulae II–V:

$X^1$ and $X^2$ are independently $NO_2$, Cl, Br, CN, $CF_3$,

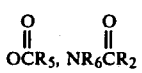

$SO_2R_2$, $SO_2NR_3R_4$, $SO_3R_2$,

or $CCl_3$ or can be H for formula III;

$Y^1$ and $Y^2$ are independently H, $NO_2$, Cl or Br; and furthermore $R_1$–$R_6$ are as previously defined;

a, b, c, d, n, m are as previously defined; and

R', R", $R^{VI}$ and $R^{VII}$ are independently H or alkyl of 1–3 carbons; and

R''', $R^{IV}$ and $R^V$ are independently H or methyl;

α-Chlorinated compounds of a more narrower scope are formed for compounds of formulae I–V where for formula I:

X is $NO_2$, Cl, Br, CN, $CF_3$,

Y is H, $NO_2$, Cl or Br;

Z is H, Cl or Br;

and for Formulae II–V;

$X^1$ and $X^2$ are independently $NO_2$, Cl, Br, CN, $CF_3$,

$SO_2R_2$, $SO_2NR_3R_4$ or $\underset{OCR_5}{\overset{O}{\underset{\|}{}}}$ or can be H for Formula III;

$Y^1$ and $Y^2$ are independently H, $NO_2$, Cl or Br; and furthermore $R_1$ is alkyl of 1–8 carbons, aryl, or alkoxy of 1–4 carbons;

$R_2$ is alkyl of 1–4 carbons;

$R_3$ and $R_4$ are independently alkyl of 1–4 carbons;

$R_5$ is alkyl of 1–8 carbons or aryl;

$R_6$ is alkyl of 1–3 carbons;

R', R", $R^{VI}$ and $R^{VII}$ are independently H or alkyl of 1–3 carbons;

R''', $R^{IV}$ and $R^V$ are independently H or methyl;

a, is 0 or 1;

b and n are 1 or 2;

c is 1;

d is 0 or 1;

m is 0–6.

α-Chlorinated compounds of a further narrower scope are formed from compounds of formula I where X is $NO_2$, Cl, CN, $CF_3$,

or $SO_2R_2$;

Y is H, $NO_2$ or Cl;

Z is H or Cl;

$R_1$ is alkyl of 1–8 carbons, aryl, or alkoxy of 1–4 carbons;

$R_2$ is alkyl of 1–4 carbons;

R', R", $R^{VI}$ and $R^{VII}$ are independently H or alkyl of 1–3 carbons;

R''', $R^{IV}$ and $R^V$ are independently H or methyl;

a is 0 or 1;

with the proviso that X=$NO_2$, Cl, or CN when a=1, Z=Cl, and Y=$NO_2$ or Cl.

PROCESS DESCRIPTION

The process of the present invention involves chlorination with dichlorine monoxide to obtain α-chlorination of a side chain of an electronegatively substituted aromatic compound provided that the net effects of substituents on the aromatic ring is electronwithdrawing. Assessment of electronwithdrawing character is well known in the art and can be derived using Hammett σ constants following the teachings of L. P. Hammett, Physical Orgainic Chemistry, McGraw-Hill, 2nd Ed, 1970, Chap. 11. or linear combination of $\sigma_I$ (polar effects) and $\sigma_R$ (pi delocalization effects) constants following the teachings of S. Ehrenson, R. T. C. Brownlee, and R. W. Taft, Prog. Phys. Org. Chem., 10, 1 (1973), A. Streitwieser, Jr. R. W. Taft, eds, John Wiley and Sons, N.Y. or M Charton, Prog. Phys. Org. Chem., 8, 235 (1971).

"α-Chlorination" in the present specification means the replacement of at least one hydrogen atom with a chlorine atom on a saturated carbon atom immediately adjacent an aromatic ring. "α-Hydrogen" refers to a hydrogen atom attached to the saturated carbon atom.

"Side chain" in the present specification means a group attached to an aromatic nucleus through a saturated carbon to which is attached at least one hydrogen atom. It is understood that the side chain can be straight or branch chained or contain a cyclic moiety or can be further linked to the aromatic nucleus at a second position.

Particular examples of suitable compounds for α-chlorination are those of formulae I to V which have been previously defined.

The α-chlorination of a side chain of an electronnegatively substituted aromatic compound through use of dichlorinemonoxide has been found to proceed normally in high yields. The chlorination is highly selective often with quantitative yields and little or no by-products from aromatic ring or other positional chlorination. The reactions are stepwise processes in which the chlorine atoms are introduced sequentially and hence use of insufficient dichlorine monoxide or termination of the reaction short of completion leads to all possible products resulting from partial and complete chlorination at the saturated carbon adjacent the aromatic nucleus. With some ortho-substituted aromatic such as substituted o-xylene compounds, incomplete replacement of all α-hydrogens by chlorine atoms may occur owing to steric factors. The extent of chlorination can be conveniently monitored by $^1$Hnmr and other analytical spectroscopy methods.

α-Chlorination of the aromatic compounds involves contacting the compound with dichlorine monoxide which is introduced into the reaction as a gas or in solution.

Due to the highly oxidative nature of dichlorine monoxide, it is necessary to dilute this chlorinating agent to avoid an explosive hazard. A diluent gas is conventionally used for this purpose when dichlorine monoxide is a gas and the type of additive can vary widely. Conventionally, the diluent gas should be inert or substantially inert to the α-chlorination to avoid introduction of by-product impurities. Diluent gases include air, nitrogen and argon although from cost considerations air is preferred. A suitable mole ratio of diluent gas to dichlorine monoxide is in a range from 1:1 to 500:1. Lower concentrations of diluent can be employed but with the hazard of increasing the explosive potential as the concentration of diluent is drastically reduced. Higher concentration than those stated can likewise be employed.

Alternatively, dichlorine monoxide can be introduced into the reaction in a solvent. A wide variety of solvents are suitable and include carbon tetrachloride, acetonitrile, methylene chloride, chloroform, trichlorofluoromethane, 1,2-dichloro-1,1,2,2-tetrafluoroethane and 1-chlorotetrafluoroethane. Acetonitrile, methylene chloride, and chloroform may react slowly with Cl$_2$O but are suitable solvents for rapid reactions. A preferred solvent is carbon tetrachloride. The concentration of dichlorine monoxide in solution is not critical. High concentration of dichlorine monoxide leads to a more rapid decomposition on prolonged storage due to a reduction in half life.

Dichlorine monoxide either in a gaseous phase or in solution is contacted with the aromatic compound as previously defined to obtain α-chlorination. The aromatic compound in a solid or molten state can directly contact the dichlorine monoxide diluted with carrier gas or solvent for this chlorination. Alternatively, the aromatic compound can be employed in solution by use of a solvent. The type of solvent will be dependent on the aromatic compound and can widely vary. If the dichlorine monoxide is also employed in solution, it is not necessary for the same solvent to be used for the aromatic compound. Hence, flexibility exists in the choice of suitable solvents for each of the reactants.

Temperatures for the α-halogenation can vary widely such as within a range from -50° C. to 250° C. and more preferably 0° C. to 150° C. Pressure is not critical since pressures above and below atmospheric pressure are suitable. For convenience, atmospheric or slightly above atmospheric is preferred. With use of a solvent, it is understood that conventionally the combination of temperature and pressure should not lead to rapid vaporization of the solvent or dichlorine monoxide. When the aromatic ring is not strongly deactivated by electron-withdrawing groups, the α-chlorination is rapid and lower temperatures are preferred at least in the early stages of reaction to prevent by-product formation. When the organic ring is strongly deactivated with electron-withdrawing groups, the reaction is generally slower and requires higher temperatures, longer reaction times or catalysis by light.

An excess of dichlorine monoxide is employed if replacement of all available α-hydrogens is undertaken. For optimum product yield, product purity and minimum reaction time, it is convenient to use excess Cl$_2$O, especially when the aromatic compound is strongly deactivated by electron-withdrawing groups.

The reaction times can vary from a few minutes to several days. The reactions are not markedly inhibited by air, small amounts of chlorine or conventional radical inhibitors. The reactions are catalyzed by diffuse light and are markedly accelerated by strong light such as a sunlamp. Normally, the presence of excess dichlorine monoxide does not lead to increased by-products. However, in reactions catalyzed by strong light, excess dichlorine monoxide may lead to by-products believed to result from substituent displacment reactions.

Water is conventionally the main by-product of the reaction and its concentration in the reaction zone is conventionally minimized. Excess water hydrolyzes Cl$_2$O in an equilibrium reaction to form hypochlorous acid.

$$Cl_2O + H_2O \rightleftharpoons 2HOCl.$$

In a water-immiscible reaction system, water is automatically separated from the reaction zone as a discrete second phase and the equilibrium reaction thus favors Cl$_2$O formation. Separation of water from the reaction zone by mechanical means, inert drying agents such as calcium nitrate or by azeotropic or conventional distillation thus favors more efficient use of Cl$_2$O. The presence of excess water and prolonged reaction times may also lead to hydrolysis of chlorinated product to ketones, acid chlorides or acid.

The electronegatively substituted aromatic compound with a side chain for α-halogenation represents a starting material in the process of the present invention. Many of the compounds are commercially available or can be prepared by modes of preparation available to one of ordinary skill in the art.

Starting materials are either known in the art or are obtainable by processes described in the literature, for example as described in:

(1) "Rodd's Chemistry of Carbon Compounds", 2nd edition, S. Coffey, ed., Vol. III, Elsevier Publishing Company, 1971.

(2) "Principles of Organic Synthesis", R. O. C. Norman, Methuen and Co., Ltd., London, 1968.

(3) "Aromatic Nucleophilic Substitution," J. Miller, Elsevier Publishing Company, 1968.

(4) "Electrophilic Substitution on Benzenoid Compounds," R. O. C. Norman and R. Taylor, Elsevier Publishing Company, 1965.

(5) "Friedel-Crafts and Related Reactions," G. A. Olah, ed., Interscience Publishers (J. Wiley and Sons), 1963.

(6) "Aromatic Substitution, Nitration and Halogenation", P. B. D. de la Mare and J. H. Ridd, Butterworths Scientific Publications, 1959.

The α-chlorinated compounds prepared by the present process using dichlorine monoxide as a chlorination agent have wide use. The α-chlorinated compounds conventionally are intermediates although some of the compounds can be directly employed without further conversion. Suitable uses of the α-chlorinated compounds are intermediates in the preparation of agricultural chemicals such as insecticides and fungicides, pharmaceuticals, antistatic agents, flame retardants, surfactants, oil additives, fuel additives, lubricants, elastomers and plasticizers.

Benzotrichlorides react with activated aromatic compounds in aqueous HF to form benzophenones. Benzophenones such as 2-chloro-5'-t-butyl-2'-hydroxybenzophenone are active as insecticides (*Chemical Abstracts* 40: 1251 c), 4-chloro-4'-phenoxybenzophenone is useful as a PVC plasticizer as taught in German patent application No. 2,451,037. This application also teaches a U.V. stabilizer utility for 4-chloro-2'-hydroxy-4'-methoxybenzophenone and teaches that related benzophenones are useful as metal complexing agents, metal extractants, dyestuffs and pharmaceuticals.

Exemplification for α-chlorinated compounds with monochlorine replacement of available α-hydrogens includes preparation of intermediate compounds, e.g., German OS No. 2,659,404 teaches that compounds such as 3-chloro-α,α-dimethylbenzyl amine, which can be derived from 3-chloro-α,α-dimethylbenzyl chloride prepared by the process of the present invention, is useful for the preparation of selective herbicides.

Exemplification for α-chlorinated compounds with dichlorine replacement of available α-hydrogens includes preparation of intermediate compounds for use as bacteriocides and fungicides as is taught in U.S. Pat. No. 3,457,310.

Exemplification for α-chlorinated compounds with trichlorine replacement of available α-hydrogens (on a single carbon) includes preparation of intermediate compounds for bactericidal and fungicidal use is taught for compounds such as 4-chloro-3-trichloromethylbenzotrifluoride in U.S. Pat. No. 3,457,310. 1,4-Bis(trichloromethyl)-benzene and related compounds are of value in improving feed conversion in ruminants as is taught in U.S. Pat. No. 3,663,710.

The following paragraphs are provided to demonstrate some of the specific uses of α-halogenated compounds prepared by the process of the present invention.

Benzotrichlorides prepared by the method of this invention are useful intermediates for the preparation of agricultural chemicals. For example, 4-chloro-3,5-dinitrobenzotrifluoride is an intermediate used in the preparation of herbicides such as trifluralin as taught in U.S. Pat. No. 3,257,190. 4-Chloro-3-nitrobenzotrifluoride finds use as an intermediate in the preparation of the miticide fentrifanil as taught in British Pat. No. 1,455,207.

Ring halogenated benzotrifluorides such as 2,4,5-trichlorobenzotrifluoride have dielectric properties which render them useful as insulating media and transformer fluids as taught in U.S. Pat. No. 2,063,979.

Nitrobenzotrifluorides such as 3,5-dinitro-2-chlorobenzotrifluoride are of value in the manufacture of azo dyes as taught in U.S. Pat. Nos. 2,194,925 and 2,212,825. Dyes related to malachite green can be prepared from 1,3-bis[trifluoromethyl]benzene as taught by G. Hallas and J. D. Hepworth in the *Journal of the Society of Dyers and Colourists*, 86, 200 (1970).

Anthracene dye intermediates accessible by the method of this invention are illustrated by 2-chloro-7-trifluoromethylanthroquinone (J. H. Simons, editor, *Fluorine Chemistry*, 248-253 (*Academic Press* 1954, New York).

Nitrobenzotrifluorides such as 3-nitrobenzotrifluoride are useful intermediates for the preparation of pharmaceuticals such as the major tranquilizer trifluoroperazine covered by British Pat. No. 813,861.

German OS No. 2,541,752 teaches that 2-carbomethoxy-5-(6)-(3-trifluoromethylphenylsulfonyloxy)-benzimidazole, a compound prepared from 3-trifluoromethylbenzenesulfonyl chloride, is useful as an anthelmintic.

Trifluoromethylphenylphosphonic acid dihalides, obtained from compounds made by the method of this invention, are claimed as intermediates for flame retardants in Dutch patent application No. 7,214,241.

Polymer intermediates such as 3-trifluoromethylstyrene, obtainable from compounds made by the method of this invention, have been prepared and polymerized as taught by G. B. Bachman and L. L. Lewis (*J. Am. Chem. Soc.* 69, 2022 (1974)).

Azo dyes such as 2-methyl-7-(trifluoromethyl)-benzomorpholine can be prepared from 4-chloro-3-nitrobenzotrifluoride as taught in U.S. Pat. Nos. 3,813,446 and 2,442,345.

The following examples illustrate but do not limit this invention. All temperatures are in degrees centigrade unless othewise stated.

Also, unles otherwise stated, analysis was by proton nuclear magnetic resonance on a Varian A60, and by high performance liquid chromatograph (HPLC) using a 50 cm×4.6 mm ID column packed with porous silica microsphere adsorbent (particle size 7μ, pore diameter 75 A, pore volume 547 cc/g) and eluted with 0.1–0.3% methanol in isooctane at 1600 psi and a flow rate of 1.54 ml/min. Fractions were determined with an Ultra Violet detector (254) nm).

EXAMPLE 1

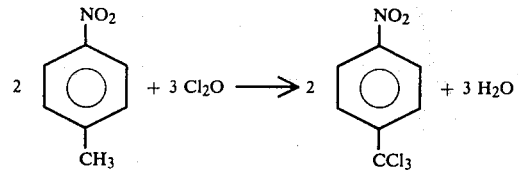

A Hastelloy pressure tube was flushed with nitrogen and charged with p-nitrotoluene (20.9 g, 0.152 mole) and dichlorine monoxide (29.14 g, 0.335 mole) dissolved in carbon tetrachloride (450 ml). The solution was heated at 75° for eight hours under autogenous pressure. The water layer was separated and the organic layer was dried (MgSO$_4$) and the solvent removed on a rotary evaporator to give a nearly colorless oil which solidified on standing to a white solid. (36.83 g, purity by HPLC 99.27%; yield 100%). The product was identified as 1-nitro-4-trichloromethylbenzene by comparison of its Hnmr and infrared spectra and high pressure liquid chromatographic retention time with an authentic sample. The product may be crystallized from petroleum ether (bp 35.8-56.5) to give substantially pure product melting at 45.8°-46.9° C.

Hnmr $\delta^{CDCl_3}$: 8.2 AB quartet (aromatic protons).
$\epsilon_{350}^{CH_3CN} = 189$.
$\epsilon_{259}^{CH_3CN} = 11,900$.

EXAMPLE 2

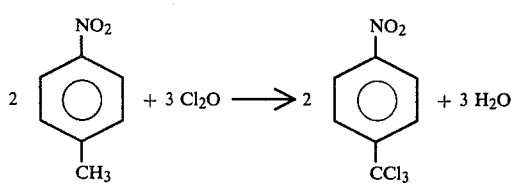

A single-neck flask was flushed with nitrogen and charged with p-nitrotoluene (33.30 g, 0.24 mole), carbon tetrachloride (30 ml) and dichlorine monoxide (42.41 g, 0.486 mole) dissolved in carbon tetrachloride (75 ml). The flask was stoppered and stored at room temperature. The solution rapidly became cloudy and a water layer separated. After 96 hours the brown color of chlorine monoxide had disappeared. The water layer was separated and the solution was filtered to separate p-nitrobenzoic acid (0.83 g). The filtrate was dried (MgSO$_4$) and the solvent removed on a rotary evaporator to give a pale yellow crystalline solid (58.80 g, purity by HPLC 99.05%; yield 99.75%), which was identified as 1-nitro-4-trichloromethylbenzene by comparison of its infrared and Hnmr spectra with an authentic sample.

EXAMPLE 3

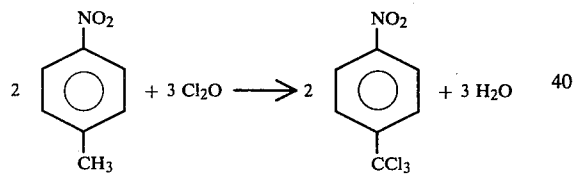

p-Nitrotoluene (1.03 g, 0.0075 mole) and dichlorine monoxide (2.5 g, 0.0285 mole) in carbon tetrachloride (48.5 ml) were added to a dry single-neck flask and stoppered. A 275 w sunlamp was placed 12" above the flask. After 1.5 hrs the reaction mixture was dried and the solvent removed on a rotary evaporator to give a pale yellow oil (1.96 g) which was shown by Hnmr and gas-liquid phase chromatography to contain unreacted p-nitrotoluene (3.32%), p-nitrobenzyl chloride (5.15%), p-nitrobenzal chloride (24.87%) and 1-nitro-4-trichloromethyl benzene (64.86%). A similar reaction run for 6.9 hrs gave a crystalline solid (2.02 g) consisting of 1-nitro-4-trichloromethyl benzene (84.37%) plus a mixture of by-products (15.67%) believed to result largely from displacement of the nitro and/or the —CCl$_3$ groups and ring substitution.

A similar reaction carried out in normal room lighting required approximately 18 hrs to give 1-nitro-4-trichloromethyl benzene (97.3%). When a similar run was carried out in total darkness the reaction required 94 hrs to give a product containing 1-nitro-4-trichloromethylbenzene 88.2%.

EXAMPLE 4

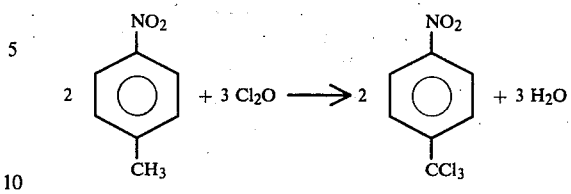

p-Nitrotoluene (1.03 g, 0.0075 mole) and dichlorine monoxide (1.37 g, 0.016 mole) in carbon tetrachloride were thoroughly mixed. The solution was divided into three equal parts and each heated in a Carrius tube at 75°. After the indicated reaction times the product was dried and the solvent removed on a rotary evaporator. HPLC analysis gave the following results.

| Time (hrs.) | Product (g) | p-Nt[1] | p-NBCl[2] | p-NBCl$_2$[3] | p-NBCl$_3$[4] |
|---|---|---|---|---|---|
| 2 | 1.88 | 0.10 | 0.29 | 2.32 | 97.36 |
| 4 | 1.86 | 0 | 0 | 0.07 | 99.93 |
| 6 | 1.87 | 0 | 0 | 0 | 100 |

[1] p-Nt = p-nitrotoluene
[2] p-NBCl = p-nitrobenzylchloride
[3] p-NBCl$_2$ = p-nitrobenzalchloride
[4] p-NBCl$_3$ = p-nitrobenzotrichloride

EXAMPLE 5

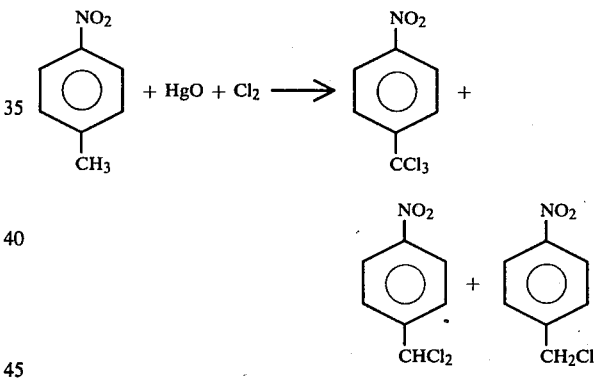

Yellow mercuric oxide (19.0 g), p-nitrotoluene (6.0 g, 0.044 mole) and carbon tetrachloride (180 ml) were stirred and heated at reflux while adding chlorine (10. g) during one hour. Heating at reflux was continued for an additional 2.5 hrs and the mixture was then stirred at room temperature for 6 days. The mixture was filtered and the solvent removed from the filtrate on a rotary evaporator to give a nearly colorless oil (9.85 g) which was identified by comparison of its Hnmr spectra and HPLC retention times with authentic samples to be a mixture of p-nitrotoluene (1.99%), p-nitrobenzyl chloride (3.95%), p-nitrobenzal chloride (17.88%), and 1-nitro-4-trichloromethylbenzene (76.19%).

EXAMPLE 6

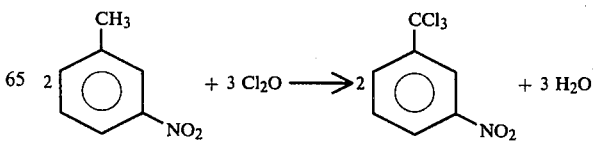

m-Nitrotoluene (3.55 g, 0.026 mole) and dichlorine monoxide (4.72 g, 0.054 mole) in carbon tetrachloride (75 ml) were added to a Carrius tube. The air was removed and the mixture heated at 75° for 6.75 hrs. The product was dried (MgSO4) and the solvent removed on a rotary evaporator to give a nearly colorless oil (6.78 g, purity by HPLC 96.79%, yield 100%). The product was combined with that from a similar run and distilled in a short path still (bath 95–100/0.1μ) to give analytically pure product ($N_D^{31}$ 1.5762).

Anal. Calcd. for $C_7H_4NO_2Cl_3$: C, 34.96; H, 1.68; N, 5.82; O, 13.31; Cl, 44.23. Found: C, 35.32; H, 1.96; N, 6.07; Cl, 44.25.

Hnmr$^{CDCl3/T}$: ω 7.69–8.88 complex group (aromatic protons).

γ$^{NaCl}$: 3.23μ, 3.42μ (trace sat.CH) weak 5.77 (>C=O impurity); 6.20μ, 6.32μ, 6.77μ (aromatic C=C; 6.55μ, 7.45μ (NO2).

EXAMPLE 7

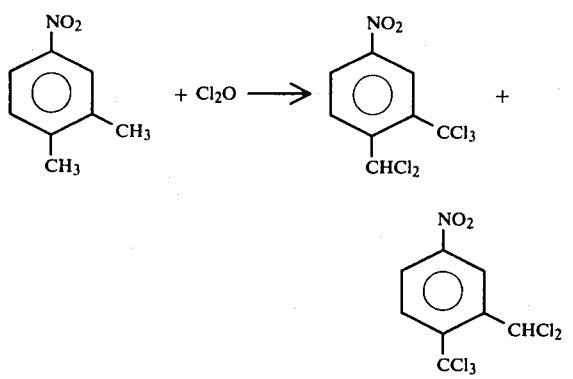

4-o-Nitroxylene (1.95 g, 0.013 mole) and dichlorine monoxide (4.72 g, 0.0543 mole) were heated at 75° for 6.75 hrs in a Carrius tube following the procedure described in Example 6. The product was dried (MgSO4) and the solvent removed to give pale yellow crystals. HPLC analysis showed the product consisted of a mixture of two compounds (47.80% and 48.86%) and minor amounts of several impurities. Hnmr analysis identified the products as 1-nitro-3-trichloromethyl-4-dichloromethylbenzene and 1-nitro-3-dichloromethyl-4-trichloromethylbenzene.

Hnmr$^{CDCl3/T}$: δ 7.79 1H singlet (CHCl2); δ 8.22–8.50 2H complex (aromatic protons); δ 8.95 1H complex (aromatic protons).

The 220 Hnmr spectra resolved the 7.79 singlet into two singlets of approximately equal weight. The two other complex groups were each resolved into two complex groups of equal weight.

EXAMPLE 8

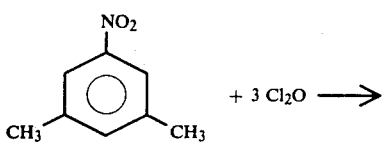

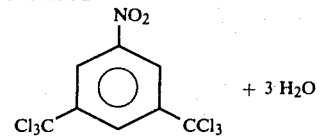

5-Nitro-m-xylene (2.15 g, 0.014 mole) and dichlorine monoxide (6.79 g, 0.078 mole) in carbon tetrachloride (70 ml) were heated in a Carrius tube as described in Example 6 at 75° for 18.5 hrs. The product was dried (MgSO4) and the solvent removed on a rotary evaporator to give a pale yellow oil (5.46 g, purity by HPLC 99.70, yield 100%). The oil was distilled in a short path still (bp ~115/0.5 mm) to give a pale yellow oil.

Anal. Calcd. for $C_8H_3NO_2Cl_6$: C, 26.85; H, 0.85; N, 3.91; O, 8.94 Cl, 59.45. Found: C, 27.39; H, 1.12; N, 3.99; Cl, 59.42.

Hnmr$^{CDCl3/T}$: δ 8.83 singlet (aromatic protons).

γ$^{KBr}$: 3.22μ (=CH); 6.18μ (aromatic C=C)); 6.47μ, 7.44μ (NO2); multiple bands in 12.5μ (CCl3).

EXAMPLE 9

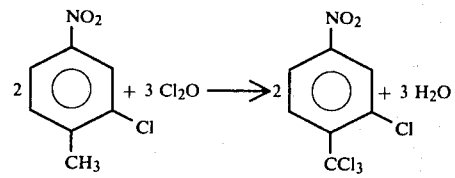

2-Chloro-4-nitrotoluene (2.19 g, 0.0128 mole) and dichloride monoxide (4.46 g, 0.0513 mole) in carbon tetrachloride (50 ml) were heated at 75°/18 hrs following the procedure described in Example 6. The product was dried and the solvent removed to give 1-nitro-3-chloro-4-trichloromethylbenzene (3.49 g, purity by HPLC 99.40%, yield 99.2%) as a pale yellow oil. The product was distikled in a short path still (bp 82–85/2μ) to give a pale yellow oil.

Anal. Calcd. for $C_7H_3NO_2Cl_4$: C, 30.58; H, 1.10; N, 5.09; O, 11.64 Cl, 51.58. Found: C, 32.22; H, 1.52; N, 5.64; Cl, 48.90

Hnmr$^{CDCl3/T}$: δ 8.5–8.8 complex group (aromatic protons).

γ$^{KBr}$: 3.22μ (=CH); 6.53μ, 7.24μ (NO2); 6.25μ, 6.30μ, 6.83μ (aromatic >C=C>). Weak 5.85μ (>C=O impurity), multiple long wave length bands concerned with CCl3.

EXAMPLE 10

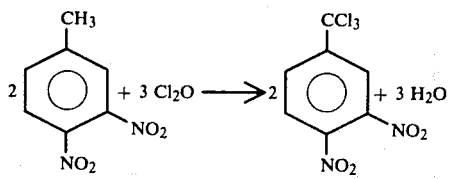

3,4-Dinitrotoluene (2.49 g 0.0136 mole) and dichlorine monoxide (4.74 g, 0.055 mole) in carbon tetrachloride (50 ml) were heated in a Carrius tube from which air had been removed, as in Example 6 at 75° for 10 hrs. The reaction solution was filtered to remove a white solid (0.35 g) which was identified by its infrared spectra as 3,4-dinitrobenzoic acid. The filtrate was dried (MgSO4) and the solvent removed on a rotary evaporator to give 1-trichloromethyl-3,4-dinitrobenzene as a white crystalline solid (3.57 g, purity by HPLC 96% yield 89.2%). The product was recrystallized from carbon tetrachloride-petroleum ether to give essentially pure product (mp 69.5°-70.6°).

An aliquot was further purified by preparative HPLC on a Water's prep. 500 silica gel cartridge. The fraction eluted with acetonitrile (0.5%) butyl chloride (25%) and cyclopentane (74.5%), was a white crystalline solid mp 70.3°-71.4°.

Anal. Calcd. for $C_7H_3N_2O_4Cl_3$: C, 29.45; H, 1.06; N, 9.81; O, 22.42; Cl, 37.26. Found: C, 29.50; H, 1.47; N, 9.72 Cl, 37.26.

Hnmr$^{CDCl_3/T}$: $\delta$ 7.9-8.6 complex group (aromatic protons).

$\gamma^{KBr}$: 3.22$\mu$, 3.26$\mu$ (—OH): 6.45$\mu$, 7.32$\mu$ 7.43$\mu$ (NO$_2$).

EXAMPLE 11

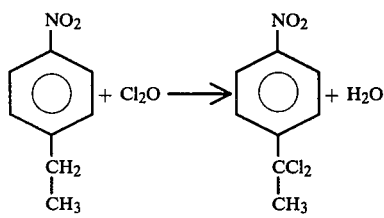

4-Ethylnitrobenzene (7.38 g, 0.052 mole) and Cl$_2$O (6.30 g, 0.073 mole) in carbon tetrachloride (75 ml) were heated in a Carrius tube as described in Example 6 at 75°.

After 10 min the solution was pale yellow indicating reaction was essentially complete. Heating was continued for a total of 8 hrs. The product was dried (MgSO$_4$) and the solvent removed on a rotary evaporator to give a pale yellow mobile oil of essentially pure 1-(1,1-dichloroethyl)-4-nitrobenzene (11.81 g) which was shown by HPLC to be 99.23% pure (yield 100%). An aliquot of the product was distilled in a short path still (0.5$\mu$, bath 100°) to give pure product (N$_D^{25}$ 1.5690.)

Anal. Calcd. for $C_8H_7NO_2Cl_2$: C, 43.66; H, 3.21; N, 6.37; O, 14.54; Cl, 32.22. Found: C, 43.65; H, 3.44; N, 6.87; Cl, 32.42.

Hnmr$^{CDCl_3/T}$: $\delta$ 2.58, 3H singlet (—CH$_3$) $\delta$7.78-8.35 4H AA'BB' pattern (aromatic protons).

$\gamma^{NaCl}$: 3.24$\mu$ (=CH); 3.34$\mu$, 3.41$\mu$, 3.49$\mu$, (sat CH); 6.22$\mu$, 6.29$\mu$ (aromatic C=C); 6.55$\mu$, 7.43$\mu$ (NO$_2$) 7.25$\mu$ (C—CH$_3$).

When the above experiment was repeated using a large excess of dichlorine monoxide (6/1 molar ratio) 1-(1,1-dichloroethyl)-4-nitrobenzene of 92.5% purity (HPLC) was obtained in 96% yield.

EXAMPLE 12

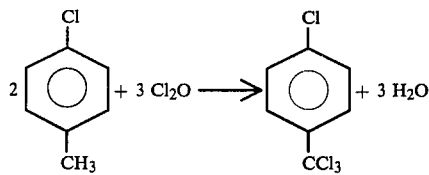

p-Chlorotoluene (1.17 g, 0.0092 mole) and dichlorine monoxide (2.40 g, 0.028 mole) in carbon tetrachloride (35 ml) were mixed and stored in a stoppered bottle at room temperature for 5 days. The initial reaction ws exothermic. The product was dried (MgSO$_4$) and the solvent removed on a rotary evaporator to give 4-chlorotrichloromethylbenzene as a pale yellow oil (2.00 g, purity by HPLC 88.78%; yield 83.9%), containing a small amount of dichlorotrichloromethylbenzene.

Hnmr$^{CDCl_3/T}$: $\delta$ 7.2-8.0 complex group (aromatic protons).

An aliquot of the product was separated on a gas liquid phase chromatography column (3% "sp2250" on 100-120 mesh Supelcoport, 6 ft. glass column, 75°-250° at 4°/min). The main product eluted at 11.09 min and was identified by its mass spectrometric pattern as 4-chlorotrichloromethyl benzene (m+228). A small fraction eluting at 13.10 min was identified in the same manner as dichlorotrichloromethylbenzene.

EXAMPLE 13

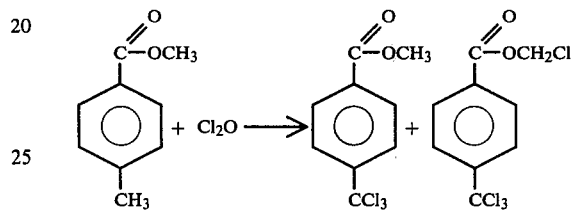

Methyl-p-toluate (4.42 g, 0.0294 mole) and dichlorine monoxide (6.40 g, 0.0736 mole) in carbon tetrachloride (75 ml) were heated in a Carrius tube at 75° for 9.5 hrs following the procedure described in Example 6. The product was dried and the solvent removed on a rotary evaporator to give a white crystalline solid consisting predominantly of methyl-p-trichloromethyl benzoate. (7.93 g composition by HPLC 69.02%; yield 73.47%), with a small amount of chloromethyl-p-trichloromethyl benzoate (7.93 g, composition by HPLC, 26.27%; yield 24.6%).

Hnmr$^{CDCl_3/T}$: $\delta$ 3.90 (—OCH$_3$), $\delta$ 6.0 (OCH$_2$Cl), $\delta$ 8.0 (aromatic protons).

An aliquot of the product from a similar run was separated on a gas-liquid phase chromatography column (3% "sp2250" on 100-120 mesh Supelcoport, 6 ft glass column, 75° C.-250° C. at 4°/min). The main product eluted at 24.32 min and was identified by its mass spectrometric pattern as methyl-p-trichloromethyl benzoate. The fraction eluting at 30.38 min was identified in the same manner as chloromethyl-p-trichloromethyl benzoate.

EXAMPLE 14

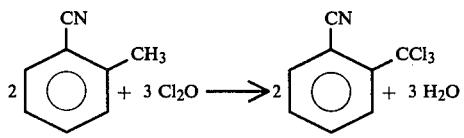

o-Tolunitrile (1.83 g, 0.0156 mole) and dichlorine monoxide (6.79 g, 0.078 mole) in carbon tetrachloride were heated at 75° for 18.5 hrs in a Carrius tube following the procedure described in Example 6. The reaction mixture was dried (MgSO$_4$) and the solvent removed on a rotary evaporator to give a white crystalline solid (4.09 g, purity by HPLC 85.45%, yield 100%). The product was combined with that of a similar run and recrystallized from cyclohexane to give substantially pure 2-trichloromethylbenzonitrile mp 98.9°-100° C.

Anal. Calcd. for C$_8$H$_4$NCl$_3$: C, 43.58; H, 1.83; N, 6.35; Cl, 48.24. Found: C, 43.86; H, 1.88; N, 6.17; Cl, 48.30.

Hnmr$^{CDCl_3/T}$: δ 7.23-8.32 complex group (aromatic protons).

γ$^{KBr}$: 3.22μ, 3.25μ (≡CH); 4.47μ (CN); 6.28μ, 6.35μ, 6.77μ aromatic C=C); muliple bands at long wave length associated with CCl$_3$.

EXAMPLE 15

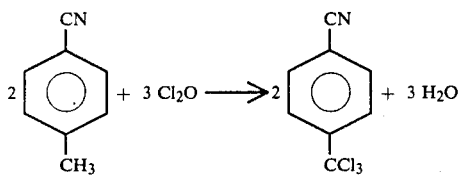

p-Tolunitrile (4.10 g, 0.035 mole) and dichlorine monoxide (6.93 g, 0.074 mole) in carbon tetrachloride (97 ml) were added to a bottle under nitrogen. The bottle was capped and stored at room temperature for 4 days. The water layer was separated, the organic layer dried (MgSO$_4$) and the solvent removed on a rotary evaporator to give p-cyanobenzotrichloride as an oil (7.87 g, yield 100%). The oil was combined with a similar run and distilled in a short path still to give a white crystalline solid which was recrystallized from petroleum ether to give substantially pure p-cyanobenzotrichloride (mp 40.5°-41.7°).

Anal. Calcd. for C$_8$H$_4$HCl$_3$: C, 43.57; H, 1.82; N, 6.35; Cl, 48.24. Found: C, 43.42; H, 1.72; N, 6.26; Cl, 47.47.

| Mass Spec | | |
|---|---|---|
| measured m/e | calculated | assignment |
| 218.9404 | 218.9409 | C$_8$H$_4$NCl$_3$ |
| 183.9730 | 183.9721 | m-Cl |

γ$^{KBr}$: 3.24μ (≡CH), 4.48μ(CN), 6.24μ and 6.67 (aromatic C=C) multiple bands at 12μ region related to ·CCl$_3$.

Hnmr$^{CDCl_3}$: δ 7.7-8.2 AA'BB' pattern (symmetrical aromatic protons).

EXAMPLE 16

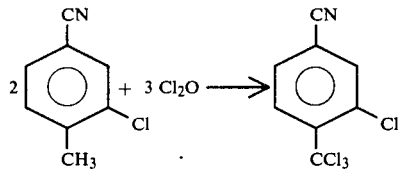

3-Chloro-4-methylbenzonitrile (3.52 g, 0.023 mole) and dichlorine monoxide (6.05 g, 0.069 mole) in carbon tetrachloride (60 ml) were heated in a Carrius tube at 75° for 24 hrs and the product isolated as described in Example 3. to give a white crystalline solid (4.0 g).

Hnmr$^{CDCl_3/T}$: δ7.59-8.42 complex group (aromatic protons).

EXAMPLE 17

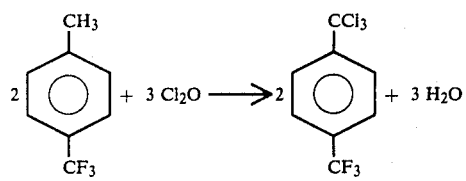

1,1,1-Trifluoro-p-xylene (2.78 g; 0.0174 mole) and dichlorine monoxide (3.32 g; 0.038 mole) in carbon tetrachloride were heated in a Carrius tube as described in Example 6 at 75° for 14 hrs. The product was dried (MgSO$_4$) and the solvent removed on a rotary evaporator to give ααα-trifluoro-α',α',α'-trichloro-p-xylene as a colorless oil (4.61 g, purity by HPLC 88.40%; yield 89%). The product was dissolved in methylene chloride, washed with 6 N NaOH dried and distilled in a short path still (bp 36°/1 mm) to give a colorless oil (3.0 g).

Anal. Calcd. for C$_8$H$_4$Cl$_3$F$_3$: C, 36.47; H, 1.53; Cl, 40.37; F, 21.63. Found: C, 36.28 H, 1.57 Cl, F, 22.05.

Hnmr$^{CDCl_3/T}$:δ7.73 AA'BB' pattern (aromatic protons).

F$^{19}$nmr$^{F11}$:-63.57 ppm, singlet (—CF$_3$).

γ$^{liquid}$:6.22μ (aromatic C=C) strong 7.5μ to 9.5μ (C—F).

EXAMPLE 18

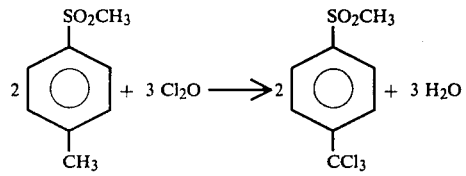

Methyl-p-tolylsulfone (4.40 g, 0.054 mole) and dichlorine monoxide (4.72 g) in carbon tetrachloride (75 ml) were heated in a Carrius tube at 75° for 6.75 hrs, as described in Example 6.

On cooling to room temperature crystals separated. The product was filtered to remove white crystals (5.99 g). The filtrate was dried and the solvent removed on a rotary evaporator to give additional crystals (1.96 g). An aliquot of the product was recrystallized once from petroleum ether to give pure 1-(methylsulfonyl)-4-(trichloromethyl)-benene (mp 168°-168.8° C.).

Anal. Calcd. for C$_8$H$_7$SO$_2$Cl$_3$: C, 35.12; H, 2.58; S, 11.72; O, 11.70; Cl, 38.88. Found: C, 35.17; H, 2.64; Cl, 38.94.

Hnmr$^{CDCl_3/T}$:δ3.12 3H singlet (CH$_3$); δ7.9-8.3 AA'BB'pattern, symmetrical aromatic protons.

γ$^{KBr}$:3.25μ (2CH); 3.35, 3.44 (sat.CH); 6.29μ (aromatic C=C); multiple bands in 7.75μ region along with 8.75μ (—SO$_2$); multiple bands in 13μ region (CCl$_3$).

| Mass Spec | | |
|---|---|---|
| measured m/e | calculated | assignment |
| 271.9264 | 271.9232 | C$_8$H$_7$O$_2$Cl$_3$S |
| 236.9538 | 236.9543 | m-Cl |
| 192.9404 | 192.9378 | m-CH$_3$SO$_2$ |

EXAMPLE 19

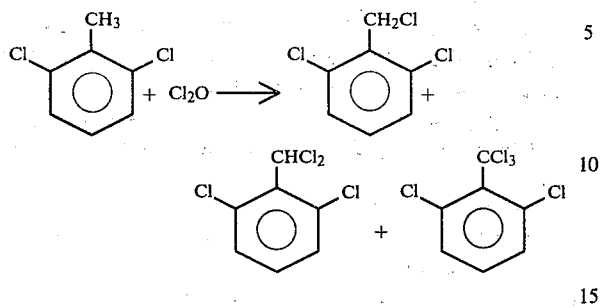

2,6-Dichlorotoluene (1.49 g, 0.0092 mole) and dichlorine monoxide (2.40 g, 0.0277 mole) in carbon tetrachloride (25 ml) were heated in a Carrius tube at 75°/20.3 hrs following the procedure of Example 6. The product was dried and the solvent removed on a rotary evaporator to give a pale yellow oil (2.84 g). The product was separated on a gas liquid chromatography column as described in Example 12. Mass spectrometric examination of the main fractions showed the product consisted largely of 2,6-dichlorobenzyl chloride, with smaller amounts of 2,6-dichlorobenzal chloride and 2,6-dichlorobenzotrichloride and isomeric products which may arise from ring substitution.

EXAMPLE 20

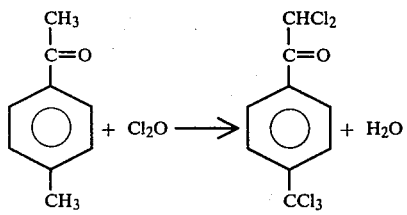

p-Methylacetophenone (1.98 g, 0.0148 mole) and dichlorine monoxide (4.17 g, 0.0148 mole) in carbon tetrachloride (50 ml) were heated in a Carrius tube at 75° for 27 hrs following the procedure of Example 6. The product was dried and the solvent removed on a rotary evaporator to give a pale yellow oil (5.05 g) consisting largely of αα-dichloro-4-trichloromethylacetophenone with smaller amounts of unidentified products (HPLC 76.2%).

Hnmr$^{CDCl_3/T}$:δ6.80 singlet

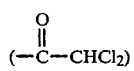

δ8.1 AA'BB' pattern (aromatic protons).

An aliquot of the product was separated by gas-liquid phase chromatography using the column described in Example 12. The main fraction was identified by its mass spectrometric pattern as α,α-dichloro-4-trichloromethylacetophenone.

EXAMPLE 21

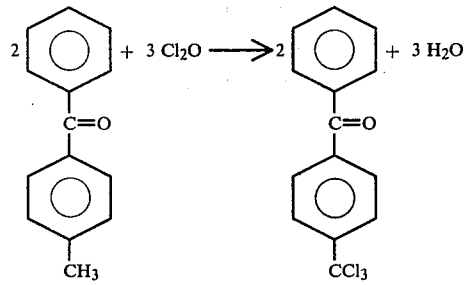

4-Methylbenzophenone (3.26 g, 0.017 mole) and dichlorine monoxide (5.77 g, 0.0664 mole) in carbon tetrachloride (60 ml) were added to a bottle. The bottle was capped and stored at room temperature for 5 days. The initial reaction was mildly exothermic and water gradually separated. The product was dried (MgSO$_4$) and the solvent removed on a rotary evaporator to give a viscous pale yellow oil (8.22 g, purity by HPLC; 76.4%; yield 100%) which crystallized on standing. The product was dissolved in carbon tetrachloride and filtered through a shallow bed of Florisil. The eluent was diluted with petroleum ether, cooled and filtered to separate a trace (~0.1 g) of low melting solid. The solvent was removed from the filtrate to give light yellow crystals (3.42 g). The Florisil was eluted with methylene chloride and the solvent removed to give additional product (2.19 g) of lower purity. The fraction eluted with carbon tetrachloride was sublimed (0.1μ/125°–140°) and recrystallized from carbon tetrachloride-petroleum ether to give pure 4-trichloromethylbenzophenone (mp 110.7–111.5).

Anal. Calcd. for C$_{14}$H$_9$OCl$_3$: C, 56.13; H, 3.03; O, 5.34; Cl, 35.50. Found: C, 56.04; H, 3.07; Cl, 35.68.

Hnmr$^{CDCl_3/T}$:δ7.22–8.28 complex group (aromatic protons).

γ$^{KBr}$:3.25μ (=CH); 6.07μ (conj ketone) 6.27μ, 6.34μ (aromatic C=C).

EXAMPLE 22

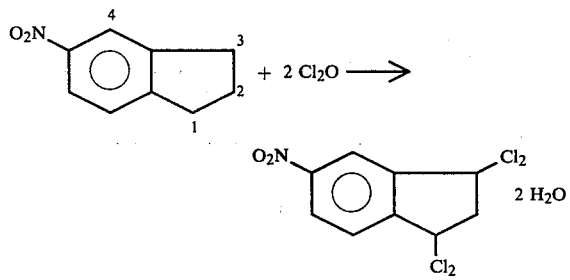

5-Nitroindan (1.14 g, 0.007 mole) and dichlorine monoxide (2.42 g, 0.028 mole) in 25 ml CCl$_4$ were heated in a Carrius tube as described in Example 6 at 75° for 18.5 hrs. The product was dried (MgSO$_4$) and the solvent removed on a rotary evaporator to give 1,1,3,3-tetrachloro-5-nitroindan as a white crystalline solid (2.10 g, purity by HPLC 97.26%, yield 97.4%). The solid was combined with a similar preparation and recrystallized from cyclohexane-petroleum ether and finally sublimed (60°/0.1μ) to give substantially pure 1,1,3,3-tetrachloro-5-nitroindan (mp 69.5–70.5).

Anal. Calcd. for $C_9H_5NO_2Cl_4$: C, 35.92; H, 1.67; N, 4.65; Cl, 47.12; O, 10.63. Found: C, 36.43; H, 1.69; N, 4.61; Cl, 47.04.

Hnmr$^{CDCl_3/T}$:δ4.03 2H singlet (—CH$_2$—); δ7.73–8.58 3H complex group (aromatic protons).

EXAMPLE 23

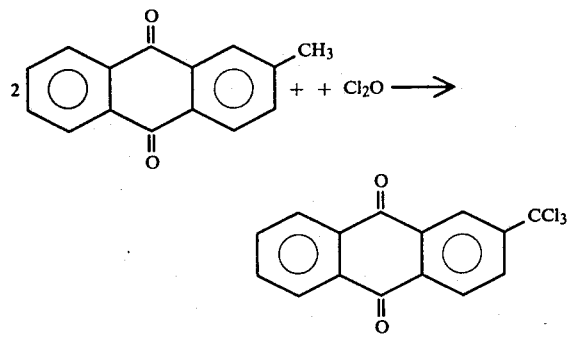

2-Methylanthraquinone (5.89 g, 0.0265 mole) and dichlorine monoxide (5.77 g, 0.0664 mole) in carbon tetrachloride (70 ml) were heated in a Carrius tube as described in Example 6 at 75° for 20.25 hrs. The product which separated as a yellow crystalline solid was dissolved in methylene chloride and filtered to separate a solid (0.49 g) judged from its infrared spectra to be anthraquinone-2-carboxylic acid. The filtrate was dried (MgSO$_4$) and the solvent removed on a rotary evaporator to give 2-trichloromethylanthraquinone as a yellow crystalline solid (8.49 g, purity by HPLC 94.26%; yield 92.5%). An aliquot of the product was recrystallized from carbon tetrachloride and then sublimed (0.1μ) to give pure anthraquinone-2-carboxylic acid, mp 157–158.2.

Anal. Calcd. for $C_{15}H_7Cl_3O_2$: C, 55.34; H, 2.17; Cl, 32.67; O, 9.83. Found: C, 55.02 H, 2.28 Cl, 33.08.

Hnmr$^{CDCl_3/T}$:δ7.68–8.82 Complex group (aromatic protons).

$\gamma^{KBr}$:3.25μ (=CH); 5.97μ (conj>C=O); 6.28μ, 6.37μ (aromatic C=C); multiple bands in 12.5μ region (CCl$_3$).

| Mass Spec | | |
|---|---|---|
| measured m/e | calcd. | assignment |
| 323.9527 | 327.9509 | $C_{15}H_7O_2Cl_3$ (mol ion) |
| 288.9808 | 288.9821 | m-Cl |
| 255.0194 | 255.0211 | $C_{15}H_8O_2Cl$ |

EXAMPLE 24

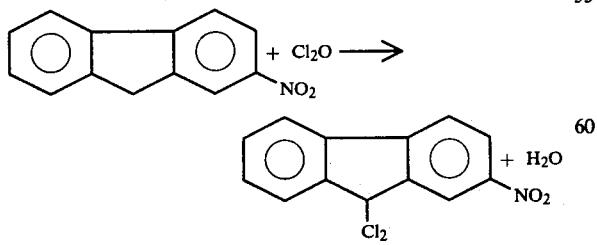

Dichlorine monoxide (4.41 g, 0.051 mole) in carbon tetrachloride (50 ml) was added to nitrofluorene (7.15 g, 0.034 mole) in carbon tetrachloride (50 ml) and the mixture was stirred at ambient temperature for 24 hrs. An initial mildly exothermic reaction resulted in a homogeneous solution which then slowly deposited a solid. The reaction mixture was dissolved in methylene chloride, dried (MgSO$_4$) and the solvent removed on a rotary evaporator to give 9,9-dichloro-2-nitrofluorene (9.60 g, purity by HPLC 63.78%, yield 64.63%).

Hnmr$^{CDCl_3/T}$:δ7.2–8.7 complex group (aromatic protons).

What is claimed is:

1. A process for α-chlorination of a side chain of an aromatic compound which comprises contacting dichlorine monoxide with an aromatic compound of the formula

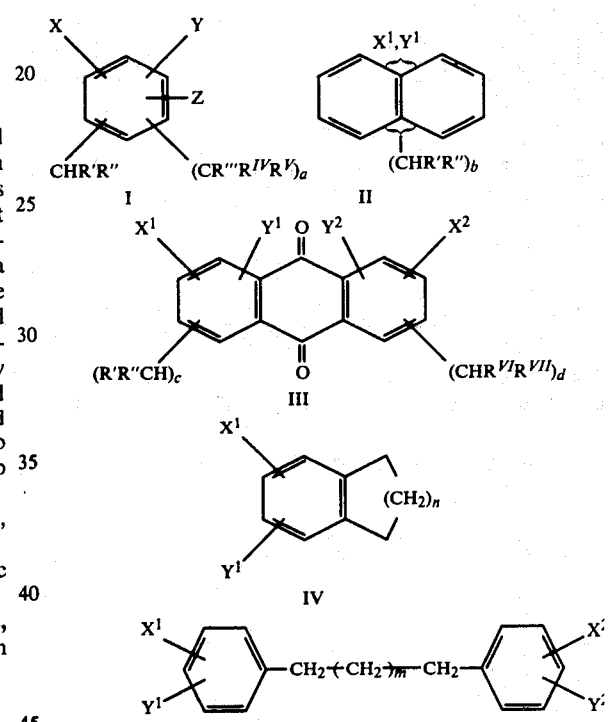

wherein for Formula I;

X is NO$_2$, CN, CF$_3$, Cl, Br, F,

$CR_1$, $SO_2R_2$, $SO_3R_2$, $SO_2CF_3$, $SO_2Cl$, $SO_2NR_3R_4$,

$OCR_5$, $\overset{\oplus}{N}(R_2)_3$, $NR_6CR_2$, $\overset{\oplus}{P}(R_2)_3$, $P(OR_2)_2$ or CCl$_3$;

Y is H, NO$_2$, Cl, Br, F, CN, CF$_3$,

$CR_{1'}$ $SO_2R_2$, $SO_3R_2$, $SO_2NR_3R_4$, $OCF_3$,

OR$_6$ or aryl;

Z is H, Cl or Br;

and for Formulae II–V:

X$^1$ and X$^2$ are independently NO$_2$, CN, CF$_3$, Cl, Br, F,

SO$_2$R$_2$, SO$_3$R$_2$, SO$_2$CF$_3$, SO$_2$Cl, SO$_2$NR$_3$R$_4$,

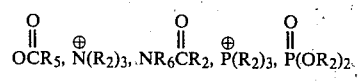

or CCl$_3$ or can be H for Formula III;

Y$^1$ and Y$^2$ are independently H, NO$_2$, Cl, Br, CN or

wherein in Formula I to V,

R$_1$ is alkyl of 1–8 carbons, aryl, alkoxy of 1–4 carbons, OH or NR$_3$R$_4$;

R$_2$ is alkyl of 1–4 carbons;

R$_3$ and R$_4$ are independently H or alkyl of 1–4 carbons;

R$_5$ is alkyl of 1–8 carbons, trifluoromethyl, or aryl;

R$_6$ is H or alkyl of 1–3 carbons; and furthermore,

R′ and R″ are independently H, alkyl of 1–3 carbons, or are joined to form a carbocyclic ring of 5 or 6 carbons; and for R″, it can also be alkyl of 1–20 carbon atoms;

R‴, R$^{IV}$ and R$^V$ are independently H or methyl;

R$^{VI}$ and R$^{VII}$ are independently H, alkyl of 1–3 carbon or are joined to form a carbocyclic ring of 5 or 6 carbons;

a is 0 or 1;

b, and c are independently 1 or 2;

n is 1 or 2; d is 0, 1, or 2; m is 0–6;

provided when X=

Y and Z both cannot be H provided when y=OR$_6$, Z cannot be H.

2. A process of claim 1 wherein for Formula I:

X is NO$_2$, Cl, Br, CN, CF$_3$,

SO$_2$R$_2$, SO$_2$NR$_3$R$_4$, SO$_3$R$_2$,

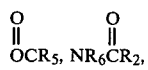

or CCl$_3$;

Y is H, NO$_2$, Cl, Br, CN, CF$_3$,

SO$_3$, R$_2$ or OR$_6$;

Z is H, Cl or Br;

and for Formulae II–V:

X$^1$ and X$^2$ are independently NO$_2$, Cl, Br, CN, CF$_3$,

SO$_2$R$_2$, SO$_2$NR$_3$R$_4$, SO$_3$R$_2$,

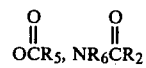

or CCl$_3$ or can be H for formula III;

Y$^1$ and Y$^2$ are independently H, NO$_2$, Cl or Br; and furthermore

R$_1$–R$_6$ are as previously defined;

a, b, c, d, n, m are as previously defined; and

R′, R″, R$^{VI}$ and R$^{VII}$ are independently H or alkyl of 1–3 carbons; and

R‴, R$^{IV}$ and R$^V$ are independently H or methyl.

3. A process of claim 2 wherein for Formula I:

X is NO$_2$, Cl, Br, CN, CF$_3$,

SO$_2$R$_2$, SO$_2$NR$_3$R$_4$ or

Y is H, NO$_2$, Cl or Br;

Z is H, Cl, Br;

and for Formula II–V:

X$^1$ and X$^2$ are independently NO$_2$, Cl, Br, CN, CF$_3$,

SO$_2$R$_2$, SO$_2$NR$_3$R$_4$ or

or can be H for Formula III;

Y$^1$ and Y$^2$ are independently H, NO$_2$, Cl or Br; and furthermore

R$_1$ is alkyl of 1–8 carbons, aryl, or alkoxy of 1–4 carbons;

R$_2$ is alkyl of 1–4 carbons;

R$_3$ and R$_4$ are independently alkyl of 1–4 carbons;

R$_5$ is alkyl of 1–8 carbons or aryl;

R$_6$ is alkyl of 1–3 carbons;

R', R", R^{VI} and R^{VII} are independently H or alkyl of 1-3 carbons;
R''', R^{IV} and R^{V} are independently H or methyl;
a, is 0 or 1;
b and n are 1 or 2,
c is 1;
d is 0 or 1;
m is 0-6.

4. A process of claim 3 wherein for Formula I X is $NO_2$, Cl, CN, $CF_3$, $$\overset{O}{\underset{}{\overset{\|}{C}}}R_1$$

or $SO_2R_2$;
Y is H, $NO_2$ or Cl;
Z is H or Cl;
$R_1$ is alkyl of 1-8 carbons, aryl, or alkoxy of 1-4 carbons;
$R_2$ is alkyl of 1-4 carbons;

R', R", V^{VI} and R^{VII} are independently H or alkyl of 1-3 carbons;
R''', R^{IV} and R^{V} are independently H or methyl;
a is 0 or 1;
with the proviso that X=$NO_2$, Cl, or CN when a=1, Z=Cl, and Y=$NO_2$ or Cl.

5. The process of claim 1 wherein dichlorine monoxide is present as a gas in combination with a diluent gas.

6. The process of claim 1 wherein dichlorine monoxide is present in solution.

7. The process of claim 1 wherein α-chlorination replaces at least one α-hydrogen of said aromatic compound.

8. The process of claim 1 wherein α-chlorination replaces all α-hydrogens of said aromatic compound.

9. A process of α-chlorination of a side chain on an electronegatively substituted aromatic compound with the proviso that the net effect of substituents on the aromatic ring is electron-withdrawing which comprises contacting dichlorine monoxide with said compound.